United States Patent [19]

Frost et al.

[11] Patent Number: 4,499,376
[45] Date of Patent: Feb. 12, 1985

[54] HYDRAULIC OIL COUNTING DEVICE AND WATER SEPARATOR

[75] Inventors: Paul T. Frost, 7746 Valle Vista Dr., Cucamonga, Calif. 91730; Robert T. Thomas, Whittier, Calif.

[73] Assignee: Paul T. Frost, Cucamonga, Calif.

[21] Appl. No.: 532,294

[22] Filed: Sep. 14, 1983

Related U.S. Application Data

[63] Continuation of Ser. No. 246,205, Mar. 23, 1981.

[51] Int. Cl.³ .................................................. G01J 1/00
[52] U.S. Cl. ..................................... 250/341; 250/343
[58] Field of Search ............... 250/301, 338, 339, 341, 250/343, 574; 356/51, 436, 441

[56] References Cited

U.S. PATENT DOCUMENTS

| | | | |
|---|---|---|---|
| 2,321,899 | 6/1943 | Dooley | 250/341 |
| 3,281,597 | 10/1966 | Greenberg | 250/343 |
| 3,600,590 | 8/1971 | Einstein | 250/574 |
| 3,917,957 | 11/1975 | Ansevin et al. | 250/343 |
| 3,962,581 | 6/1976 | Zimmerman | 250/341 |
| 4,045,671 | 8/1977 | Dille et al. | 250/341 |
| 4,229,653 | 10/1980 | Uthe | 250/339 |

*Primary Examiner*—Janice A. Howell
*Attorney, Agent, or Firm*—Boniard I. Brown

[57] ABSTRACT

Apparatus for measuring the quantity of opaque material within a fluid stream which includes apparatus for directing an associated fluid stream. A beam of infrared light extends through the associated fluid and means are provided for sensing the intensity of the beam of infrared light after passing through the associated fluid. Means is also provided for producing a signal which is a function of an output of the means for sensing.

3 Claims, 1 Drawing Figure

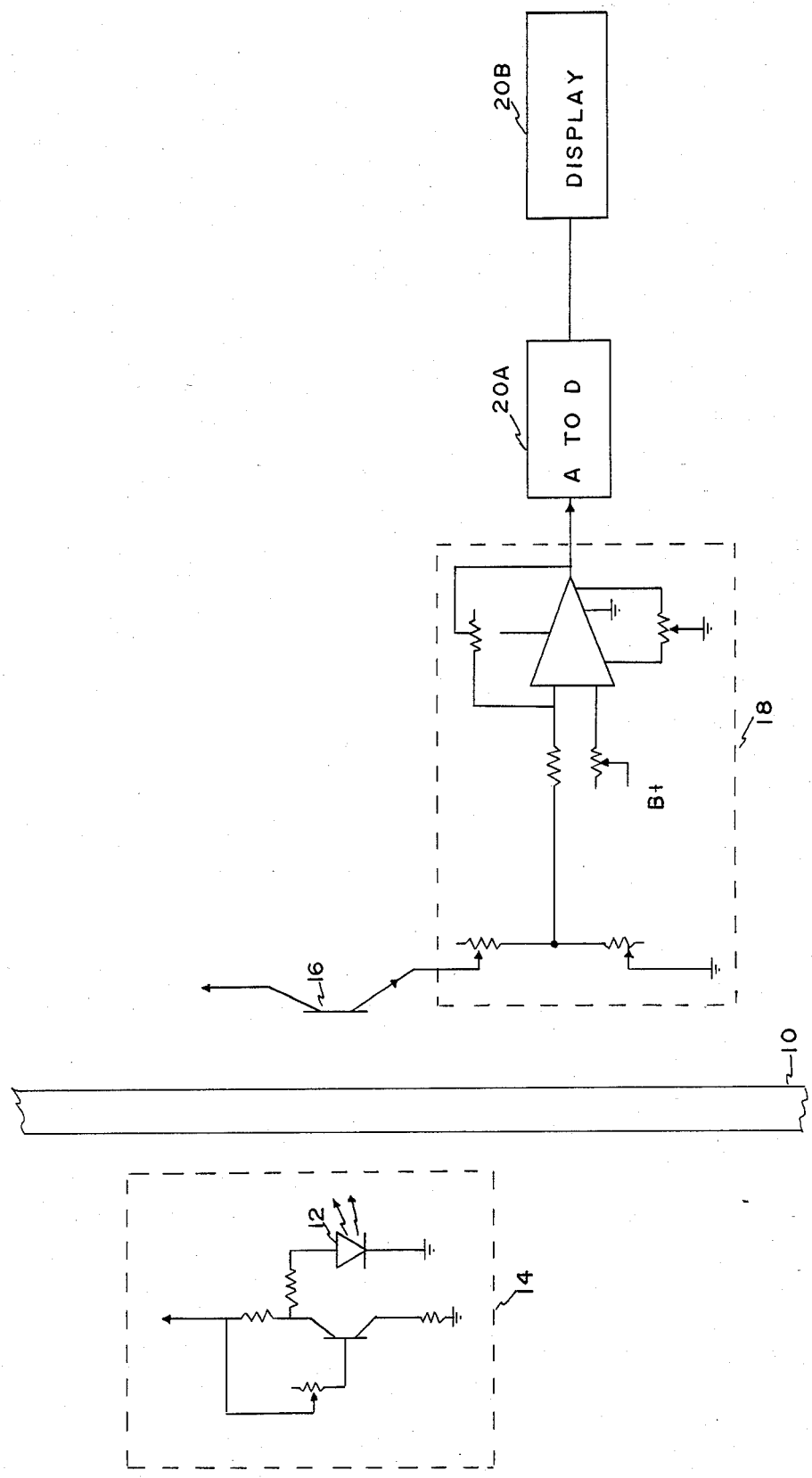

HYDRAULIC OIL COUNTING DEVICE AND WATER SEPARATOR

This is a continuation of co-pending application Ser. No. 06/246,205 filed Mar. 23, 1981.

BACKGROUND OF THE INVENTION

The invention relates to means for detecting particles suspended in a fluid medium. While the invention has particular application for use with hydraulic fluids it will be understood that it also has application to other fluids. The apparatus in accordance with the invention may be used advantageously with expensive hydraulically operated machinery. Applications include machinery used in the military, aerospace, machine tool, earth moving, and other commercial fields. Such machinery, in addition to being relatively expensive, often will have high requirements for reliability and minimizing wear of the associated hydraulic system and often represents a large capital investment. A malfunction of such machinery may seriously delay the performance of other parts of a project. For example, earth moving equipment may be required to function on schedule in order to complete a critical part of a project, so that other parts may be completed. In many other applications, the consequential effects of commercial, military or aerospace equipment failing may be very significant.

Various devices are known for such applications. Much of the equipment of this type is relatively delicate laboratory type equipment which is not wholly satisfactory for field applications. In addition, much of the prior art apparatus is expensive and accordingly has not been widely accepted commercially.

One reason for the relatively great expense of the earlier apparatus is that they have in many cases utilized a relatively expensive and complicated lens system.

Such apparatus is shown in U.S. Pat. No. 2,789,765, which includes apparatus which requires scanning by an electron beam to produce signals in a manner similar to that employed in some television cameras. Other structures are shown in U.S. Pat. Nos. 2,656,508; 2,379,158; 2,791,377; 2,791,697; and 2,791,150.

It is a primary object of the invention to provide apparatus which will indicate the presence of matter such as contamination in a fluid and which will function in typical military, aerospace and commercial environments.

It is another object of the invention to provide apparatus which will improve the reliability and reduce maintenance costs of the cooperating hydraulic equipment.

It is another object of the invention to provide apparatus which is portable.

Another object is to provide apparatus which may be used independently to permit checking of hydraulic reservoirs in different hydraulically operated equipment or may be assembled as an integral part of a piece of machinery or of mobile equipment.

Yet another object of the invention is to provide apparatus which is simple in design and thus easy and inexpensive to manufacture.

SUMMARY OF THE INVENTION

The foregoing objects and other objects and advantages which shall become apparent from the detailed description of the preferred embodiment are attained in an apparatus for measuring the quantity of opaque material within a fluid stream which includes means for directing an associated fluid in a stream. Means are provided for producing a beam of infrared light and passing the beam through the associated fluid in the means for directing together with means for sensing the intensity of the beam of infrared light passing through the fluid which is produced by the means for generating. The apparatus may include means for producing a signal which is a function of an output of the means for sensing.

The means for sensing may include a photo-transistor. The means for producing a signal may include means for producing an analog signal and an analog to digital converter. The apparatus may also include a visual display indicative of the quantity of infrared light passing through the stream of associated fluid. The visual display may include a digital display. The means for directing may comprise a fluid conduit having at least portions of the walls thereof constructed of a material which allows a passage of infrared light.

The means for producing a signal may produce a signal having arbitrarily selected units to indicate the quantity of liht which passes through the associated stream of fluid. The units vary between 0 and 100.

BRIEF DESCRIPTION OF THE ACCOMPANYING DRAWING

The drawing shows a schematic view of one form of the apparatus in accordance with the invention.

DESCRIPTION OF THE PREFERRED EMBODIMENT

Referring now to the drawing there is shown a tube 10 having walls manufactured of a material which allows the passage of infrared light. Infrared light will be understood to refer to the band of electromagnetic wavelengths lying between the extreme of the visible (about 0.75 microns) and the shortest microwaves (about 1000 microns). The inventors of the present apparatus have found that infrared radiation is particularly desirable for quantitative measurements of the presence of contamination and other relatively solid matter within a fluid. More particularly, the infrared light will pass through fluids, including liquids where visible light will not pass. Visible light tends to disperse more rapidly and thus produce transient signals.

On one side of the conduit 10 is disposed a light emitting diode 12 which is part of a commercially available infrared transmitter, part #L33007, manufactured by Scan-O-Matic, Inc., Racine, Wisc. This equipment includes various adjustments to vary the intensity of the infrared radiation produced by the light emitting diode 12.

A commercially available receiver or phototransistor apparatus 16 (part #P33001, also manufactured by Scan-O-Matic) is disposed on the opposite side of the conduit 10. Means (not shown) may be provided to allow only light transmitted by the transmitter 14 and which passes through the conduit 10 to reach the receiver 16. The phototransistor 16 is of a type which is sensitive to infrared light. The gain of the differential operational amplifier 18 is controlled for a high calibration point with the input to the operational amplifier 18 controlled with a low point of calibration. The inverted output of the operational amplifier 18 is then fed to a single chip digital display 20. Schematically this is shown as two discrete blocks 20A and 20B. The first block 20A is a D to A converter and the second block being a digital display unit. In practice the single chip 20 contains both the circuitry to convert the analog signal to a digital value and the display elements. Such apparatus is sold by Digital Equipment Corporation, Tucson, Ariz. and has a part number designation of B5X102.

The convention is followed in the drawing of identifying the supply voltage with the legend "V".

It has been found that the apparatus will function to sense particles which are 50 microns in size or smaller. The apparatus may be utilized with hydraulic systems of various other apparatus. When used in this manner, the apparatus will filter a quantity of hydraulic fluid, taken from the hydraulic reservoir, through special filters until a predetermined standard is satisfied. For example, the standard might be that the contamination should be less than 40 microns. The apparatus may also be permanently assembled as an integral part of a single hydraulic system. The apparatus has been found to be durable enough so that it may be installed permanently on a piece of equipment such as a military tank, aircraft or building construction equipment.

The digital display 20B is provided with arbitrary units of 0–100. The absolute digital value has no specific meaning and is merely an arbitrary scale to approximate the degree of contamination in a hydraulic fluid, or in the case of other fluids to indicate the presence of solid matter. Ordinarily when a 0 level is achieved on the digital display this is indicative that the fluid may have a contamination level of approximately 20,000 parts/million at a micron level of 5–15.

It will be understood that the infrared light is particularly advantageous because it will penetrate fluids and particularly liquids where visible light will not penetrate. The use of visible light also results in rapid dispersion of the light and this in turn results in many transient signals at the receiver and thus relatively unstable and unreliable indications.

The apparatus avoids a common problem, in that the user of a hydraulic system does not have any convenient and cost effective way to determine the extent of contamination in the hydraulic fluid of his system. Although the apparatus does not provide exact particle count in a given fluid sample, to do so would cause inordinate complexity of the system, and also radically increase the cost. Such a system would also be substantially more fragile.

The path for the infrared light passing from the transmitter 14 to the receiver 16, may include a "window" through the conduit 10 so that the path of the infrared light from the transmitter 14 to the receiver 16 is more clearly defined. The "window" (not shown) will in other words limit the axial extent of the conduit 10 through which light may pass. Obviously, in some fluids, the presence of solid matter may not be deemed to be contamination as such. The apparatus has application for measuring matter which is opaque to infrared light in a wide variety of applications. This includes dust clouds and blood cell counting.

The invention has been described with reference to its illustrated preferred embodiment. Persons skilled in the art of constructing hydraulic counters may, upon exposure to the teachings herein, conceive variations in the development of the components therein. Such variations are deemed to be encompassed by the disclosure, the invention being delimited only by the appended claims.

We claim:

1. Apparatus for measuring particulate contamination in a liquid as a function of infrared opacity comprising:
   infrared radiation source means providing non-monochromatic, relatively wide bandwidth infrared radiation comprising light emitting diode means;
   conduit means containing a representative amount of the liquid, the conduit means having a portion thereof optically connected to the infrared light source means such that the infrared light therefrom passes through a first section of the portion into the liquid and out of the portion through a second section, said first and second sections being substantially transparent to the infrared light;
   infrared sensing means sensitive to the relatively wide bandwidth infrared radiation from the infrared radiation source optically connected to the second section providing an electric analog signal as a function of the amount of infrared radiation received by the sensing means; and,
   output means comprising linear amplifier means calibrated for at least one signal level from the sensing means for a known infrared radiation level, analog-to-digital converter means connected to the output of the amplifier, and output meter means connected to the analog-to-digital converter such that a digitally displayed indication of the amount of infrared radiation received by the sensing means is provided, thereby supplying an indication of the infrared opacity of the liquid.

2. The apparatus of claim 1 wherein the infrared sensing means is an infrared sensitive phototransistor.

3. The apparatus of claim 1 wherein the liquid is a hydraulic fluid.

* * * * *